United States Patent [19]
Raheman et al.

[11] Patent Number: 5,851,534
[45] Date of Patent: Dec. 22, 1998

[54] METHODS FOR PREVENTION AND/OR TREATMENT OF NEUTROPENIA

[75] Inventors: Fazal Raheman, Burlington; Nicolae Istrate, Lexington; Gita Muni, North Reading; Edgard Brauner, Brighton, all of Mass.

[73] Assignee: Dynagen, Inc., Cambridge, Mass.

[21] Appl. No.: 642,425

[22] Filed: May 3, 1996

[51] Int. Cl.$^6$ .................................................. A61K 39/108
[52] U.S. Cl. .................... 424/260.1; 436/71; 536/123.13
[58] Field of Search ........................... 436/71; 424/243.1, 424/260.1, 244.1; 536/123.13

[56] References Cited

U.S. PATENT DOCUMENTS 4,182,751  1/1980  Ayme ......................................... 424/92

OTHER PUBLICATIONS

Cruse et al. 1997 *Illustrated Dictionary of Immunology*. CRC Press. N.Y. pp. 72–73.
Olinescu, A., et al., "Normal Immune Functions Consequent to Cantastim Therapy in a Case of Chronic Lymphatic Leukemia T CLLT", *Rev IG Bacteriol Virusol Parazitol Epidemiol Pneumoftiziol Ser Bacteriol Virusol Parazitol Epidemiol*, (1988) 33:3:281–288.
Negut et al. Arch. Roum Path. Exp. Microbiol. 1985. 44(4):323–335.
Olinescu et al. Neoplasm. 1991. 38(1):119–128.
Likhite (Exp. Cancer Immunother. 1976 pp. 985–989.)
Antony et al. J Clin. Invest. 1985. 76:1514–1521.
Jackson et al. J. Clin. Pathol. 1994 76:1514–1521.
Oanforth et al. Clin. Immunol. Immunopath. 1995. 74(1): Abstract Only.
Usani et al. Br. J. Cancer. 1988. 57:70–73.
O Shima et al. Zbl. Bakt. 1991. 275: 374–381.
Keller et al. Infect. & Immun. 1992. 60(9):3664–3672.
Kusonoki et al. J Exp. Med. 1995. 182: 1673–1682.

*Primary Examiner*—James C. Housel
*Assistant Examiner*—Jennifer Shaver
*Attorney, Agent, or Firm*—Wolf, Greenfield & Sacks, P.C.

[57] ABSTRACT

The present invention is directed to a method of treating individuals exhibiting neutropenia or at risk of neutropenia. The method comprises the step of administering to an individual exhibiting neutropenia or at risk of neutropenia, an effective amount of a colony modulating factor derived from bacteria. The colony factor modulator exhibits an immunomodulating effect in humans and promotes a stabilization or increase in neutrophil count.

18 Claims, 2 Drawing Sheets

METHODS FOR PREVENTION AND/OR TREATMENT OF NEUTROPENIA

FIELD OF INVENTION

This invention pertains to the field of immunopharmacology and, in particular, the use of a colony modulating factor derived from bacteria to modulate the neutrophil counts of individuals affected with hemopoietic disorders.

BACKGROUND

The erythrocytes, leukocytes and platelets constitute the essential elements of the human hemopoietic system. The primary function of erythrocytes is to transport hemoglobin, which in turn carries oxygen from the lungs to tissues. The oxygenated hemoglobin gives the erytlirocytes a red color. Such cells are also known as red blood cells, or RBCs. The leukocytes comprise granulocytes, monocytes, and lymphocytes. These cells are not naturally pigmented. Such cells are whitish or transparent in appearance and are known as the white blood cells, or WBCs. These cells provide protection against various pathogens.

Five different types of white blood cells are normally found in the blood. These are polymorphonuclear neutrophils, polymorphonuclear eosinophils, polymorphonuclear basophils, monocytes and lymphocytes. In addition, there are large number of platelets which are fragments of a sixth type of white cell found in the bone marrow, the megakaryocyte. The three types of polymorphonuclear cells have a granular appearance to their cytoplasm, they are therefore called as granulocytes.

The granulocytes and the monocytes protect the body against invading pathogens mainly by ingesting them, a process called phagocytosis. These cells are transported to areas of serious inflammation to seek out and destroy any foreign invader. Neutrophils and monocytes can squeeze through the pores of the blood vessels by the process of diapedesis. Once in the tissue, they are attracted towards the pathogen by chemotaxis and move through the tissue by ameboid motion. The neutrophils are mature cells that can attack and destroy bacteria and viruses even in the circulating blood. The monocytes after reaching the tissue get enlarged and convert into macrophages.

All of these white blood cells originate in the bone marrow from an undifferentiated progenitor cell called the "pluripotent stem cell." A stem cell is one which is capable of both self-renewal and differentiation. The pluripotent stem cell has the morphologic characteristics of a mature lymphocyte.

The control of stem cell proliferation into differentiated cell types is still not completely understood. Recent insights into the precise role of various cytokines in stimulating differentiated cell lines has provided a basis for developing treatment strategies for leukopenia, agranulocytosis, or neutropenia.

Leukopenia is a condition characterized by lower than normal levels of leukocytes in the peripheral blood. Agranulocytosis is a condition characterized by lower than normal levels of granulocytes in the peripheral blood. Neutropenia is a condition characterized by lower than normal levels of neutrophils in the peripheral blood. Mean normal neutrophil counts for healthy adults are on the order of 4400 cells/$\mu$L, with a range of 1800–7700 cells/$\mu$L. A count of 1,000 cells to 500 cells/$\mu$L is moderate neutropenia and a count of 500 cells/$\mu$L or less is severe neutropenia. In individuals exhibiting normal blood cell counts, neutrophils constitute approximately 60% of the total leukocytes. (Ref: Harrison's Principles of Internal Medicine, 11th ed, Eugene Braunwald, M.D., et al., eds; McGraw-Hill; New York, 1987).

Individuals with neutrophil counts of 1,000 to 1,500 will normally exhibit no significant propensity for infection. These individuals, in the presence of infection, may exhibit fevers which can be managed on an outpatient basis. Individuals with moderate neutropenia may exhibit a propensity to infection. These individuals may exhibit fevers in the presence of infection which are difficult to manage. Individuals with severe neutropenia exhibit a significant propensity to infection. These individuals exhibit fevers in the presence of infection that are normally managed on an inpatient basis with antibiotics.

Typically, in leukopenia, agranulocytosis or neutropenia, the bone marrow stops producing the particular white blood cells. The low levels of these particular white blood cells leaves the body unprotected against bacteria and other agents that might invade the tissues.

Normally, the human body is constantly exposed to large numbers of bacteria. The mucous membranes of mouth, gastrointestinal, respiratory and genitourinary tracts are inhabited with large number of pathogens. A decrease in the number of white blood cells results in invasion of the tissues by these pathogens that are already present in the body. If the bone marrow stops producing white blood cells for 48 hours, ulcers may appear in mouth or lower intestine, or severe respiratory infection may develop. The bacteria may invade the surrounding tissue and blood. Without treatment, death ensues 3 to 6 days after acute total leukopenia begins.

Malfunction in the production of erythrocytes can also be serious, causing anemia and tissue hypoxia and consequent death. In bone marrow aplasia, no cells of any type (neither white blood cells nor red blood cells) are produced in the bone marrow. This clinical condition is termed as aplastic anemia. Total bone marrow aplasia or various degrees of myelosuppression are commonly a consequence of gamma irradiation caused by a nuclear explosion, therapeutic exposure to radiation, or cytotoxic drug treatment. Chemicals containing benzene or anthracene and even some commonly used drugs like chloramphenicol, thiouracil and some barbiturate hypnotics can cause myelosuppression resulting in aplastic anemia, or agranulocytosis, or neutropenia.

The principal factor that stimulates red blood cell production is a circulating hormone called erythropoietin, a glycoprotein with a molecular weight of about 34,000 D. Erythropoietin is now widely used as a drug for the treatment of anemia resulting from renal failure or cancer chemotherapy.

The white blood cells are unresponsive to erythropoietin and require other stimulating factors. The stem cells of myeloid lineage require colony stimulating factors (CSFs) for their further proliferation and maturation into granulocytes or monocytes. Myeloid stem cells of granulocyte lineage require granulocyte-colony stimulating factor (G-CSF). Myeloid stem cells of granulocyte, as well as monocyte lineage require granulocyte macrophage-colony stimulating factor (GM-CSF).

Both G-CSF and GM-CSF are approved as drugs for treating neutropenia resulting from myelosuppression. Although currently available CSF based therapies for neutropenia are effective in elevating the neutrophil counts, they are not devoid of shortcomings.

The CSF treatment should be closely monitored with frequent complete blood count (CBS) measurements to prevent overstimulation of the granulocytes. Over stimulation of peripheral blood cells may result in granulocytosis or even polycythemia.

CSF therapies are very expensive. So expensive that even in industrial countries many patients with myelosuppressive conditions cannot afford treatment.

There presently exists a need for an improved therapy for restoring or normalizing the peripheral blood cell population. Ideally, the therapy should prevent or limit neutropenia in individuals at risk for developing neutropenia or experiencing clinical conditions associated with neutropenia.

Such therapy for neutropenia treatment or prevention should be easy and safe to administer, self-limiting, and require few diagnostic tests to follow the course of treatment. Such therapy should be affordable. Such a therapy would reduce the health care costs. The patient should be able to take the treatment on ambulatory basis, thereby reducing the hospital visits while still enjoying a better quality of life. Such therapy should maintain the productivity of the individual.

SUMMARY OF THE INVENTION

The present invention is directed to a method of treating individuals with neutropenia or at risk of developing neutropenia. The method comprises the step of administering to an individual with neutropenia or at risk of developing neutropenia, an effective amount of a colony modulating factor (CMF) which colony modulating factor is derived from bacteria. The colony modulating factor promotes a normal range of neutrophils as a percentage of the total blood cell populating the subject.

Colony modulating factors are derived from the outer membrane and a cell wall of bacterial cell surface layers. Colony modulating factors comprise a mixture of lipids, including glycolipids and/or phospholipids.

Preferably, the colony modulating factor is derived from at least one bacteria selected from the group consisting of *Mycobacteria tuberculosis bovis, Brucella abortus, Corynebacterium parvum, Escherichia coli, Klebsiella pneumoniae. Neisseria catarrhalis, Nocardia, Proteus mirabilis, Pseudomonas aeruginosa, Staphylococcus aureus, Streptococcus* (*pyogenes, viridans fecalis, pneumoniae*) and *Bacillus subtilis*. A preferred *Mycobacteria tuberculosis bovis* strain is Bacillus Calmette Guerin strain (BCG).

A preferred colony modulating factor is a mixture of lipids. A preferred gram-negative bacteria is *Pseudomonas aeruginosa*. A preferred *Pseudomonas aeruginosa* strain is strain 4922. A preferred lipid mixture is comprised of glycolipids and/or phospholipids. A preferred lipid mixture, derived from *Pseudornonas aeruginosa*, is sold under the trademark "Cantastim". This product is characterized as a mixture of glycolipids and/or phospholipids. Biological activity is believed related to one or more lipid components.

The lipid extract may be further purified to remove components which do not participate in the immunomodulating effect. The active components of the extract can be chemically synthesized or made by recombinant means.

As used herein, an "effective amount of a colony modulating factor" refers to an amount of such extract which when administered orally, subcutaneously, intramuscularly, intravenously, by aerosol to the respiratory tract, intradermally, or rectally, induces a biological response in the individual. Such response is manifested by a stabilization or improvement in immune system function and, in particular, neutrophil counts.

An effective amount of a colony modulating factor lipid extract derived from *Pseudomonas aeruginosa* is 0.1–10.0 mg. Preferably, the amount is in the range of 0.5–1.0 mg. Preferably, the effective amount is administered more than once. Preferably, the effective amount is administered every day to every thirty days and, more preferably, every five to fifteen days. This regimen can be maintained for up to six months to one year, or even the life of a subject. Preferably, the effective amount is administered weekly for up to fifty-two weeks; more preferably, for one to thirty-two weeks, and even more preferably, for four to fourteen weeks.

Preferably, after a period of administration of the colony modulating factor, the therapy is discontinued for four to 52 weeks and restarted. Even more preferred, the therapy is restarted after eight to fourteen weeks. In some cases, lifelong treatment may be indicated.

A preferred manner of administration of the lipid for prevention of neutropenia in subjects on myelosuppressive drugs, for example, in the case of chemotherapy for some cancers, is 0.5–1.0 mg, subcutaneously, weekly for 24 weeks. Preferably, the first dose of CMF is either administered the same day or 48 hours before the myelosuppressive drug. The colony modulating factor is administered with the subsequent chemotherapy cycles, usually occurring at monthly intervals.

The effective amount, 0.5–1.0 mg, of colony modulating factor is usually administered in a solution suitable for subcutaneous administration. A typical solution for administration contains 0.5–1.0 mg/ml with suitable preservatives, stabilizers, and buffers.

Embodiments of the present invention provide a cost-effective therapy for treatment and/or prevention of neutropenia. Individuals are at risk for developing neutropenia or typically exhibit neutropenia in several clinical situations. Individuals may exhibit neutropenia after bacterial or viral infection. Post infectious neutropenia can start within a few days of the onset of the infection and last several weeks. Examples of viral and bacteria agents which give rise to neutropenia comprise varicella, measles, rubella, hepatitis A and B, infectious mononucleosis and influenza, humaimmunodeficiency virus (HIV), brucellosis, tularemia, rickettsia, and M. tuberculosis.

Individuals may exhibit drug induced neutropenia following administering of antineoplastic agents or other drugs which suppress bone marrow. Such drugs include phenothiazines, semisynthetic penicillins, nonsteroidal anti-inflammatory agents, aminopyrine derivatives, and antithyroid medication.

Neutropenia may be associated with immunologic abnormalities, (autoimmune neutropenia), metabolic diseases, hypersplenism, and nutritional deficiencies.

Subjects receiving colony modulating factors exhibit fewer opportunistic infections and consequently demonstrate better response to the chemotherapy or other therapy for infectious diseases. Such individuals use less hospitalization and exhibit an overall improvement in general clinical condition. When administered to the individuals who experience autoimmune neutropenia, hypersplenism, some metabolic diseases and some nutritional deficiencies, the development of fatal infection with nonpalhogenic bacteria can be prevented. These individuals perceive an improvement in the quality of life. The preferred colony modulating factor is well tolerated and can be administered with concurrent G-CSF or GM-CSF use.

The preferred colony modulating factors of the present invention can be produced without sophisticated chemical synthesis. Thus, the present invention can be made widely available in developed as well as in the developing countries.

These and other benefits will be apparent to individuals skilled in the art as described more fully in drawings and detailed description.

DETAILED DESCRIPTION OF THE INVENTION

Figure 1:
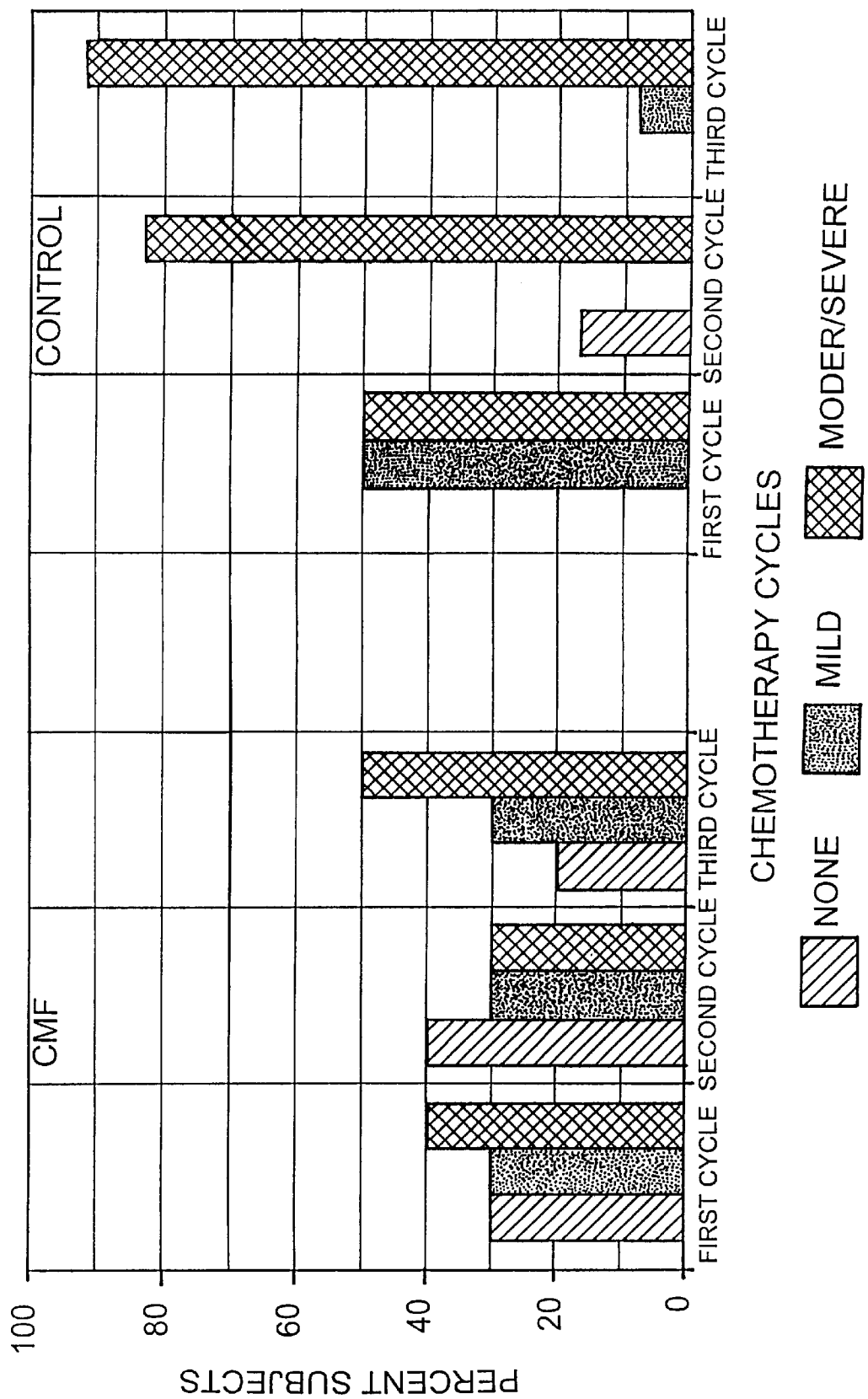
FIG. 1 depicts, in bar graph form, neutropenia ratios in cancer chemotherapy patients receiving colony modulating factor therapy in accordance with the present invention.

The present invention will be described in detail as a method of treating individuals with neutropenia, or at risk of having such disorders. As used herein, "at risk" refers to individuals who have a high probability of acquiring or developing neutropenia. For example, a patient with malignant tumor who is prescribed chemotherapeutic treatment. These treatments frequently lead to varying degree of myelosuppression. The method comprises of the step of administering to an individual with or at risk of neutropenia, an effective amount of a colony modulating factor.

Colony modulating factors are comprised of a mixture of glycolipids and/or phospholipids. The colony modulating factor is preferably derived from at least one bacteria selected from the group consisting of *Mycobacteria tuberculosis bovis, Brucella abortus, Corynebacterium parvum, Escherichia coli, Klebsiella pneumoniae, Neisseria catarrhalis, Nocardia, Proteus mirabilis Pseudomonas aeruginosa, Staphylococcus aureus, Streptococcus* (*pyogenes, viridans, fecalis, pneumoniae*) and *Bacillus subtilis*. A preferred *Mycobacteria tuberculosis bovis* is bacillus Calmette Guerin strain (BCG).

A preferred colony modulating factor is a mixture of lipids, preferably glycolipids and/or phospholipids. A preferred gram-negative bacteria is *Pseudomonas aeruginosa*. A preferred strain of *Pseudomonas aeruginosa* is strain 4922. A preferred lipid extract is sold under the trademark "Cantastim". This extract is made by in accordance with the methods described in Marx, A., Petcovici, M.: "Immunochemical Studies on Purified Common Enterobacterial Antigen (Kunin)", *Zbl. Bakt. Hys.* 1 Hbt Orig., 233 1975 486.

In brief, 30 L of meat extract are mixed with the required quantity of meat peptone in order to obtain 900 mg proteic nitrogen/L. Sodium chloride is added to a final concentration of 7.5 g/L and the pH is adjusted to 7.5. Distilled water is added to 120 L. The medium is sterilized at 110° C. for 30 minutes in a bioreactor, previously sterilized with water (120° C., 30 minutes).

*Pseudomonas aeruginosa* lyophilized strain (Cantacuzino Institute No: 4922) is dispersed on four tubes of inclined agar and cultured for 20 h at 37° C. The preinoculum is inoculated into 3000 ml of culture medium and cultured for 18 h at 37° C. with stirring (250 rpm) on a rotary shaker.

This inoculum is then introduced into the 120 L culture broth in the bioreactor. The culture medium is maintained at 37° C. for 16 h with stirring (250 rpm) and aeration (8000 L/h).

Following culture, the resultant cell suspension is centrifuged (7000 g). The supernatant is sterilized (120° C., 30 minutes) and discarded.

The bacterial mass obtained following centrifugation (usually: 2000–3000 g) is suspended in acetone (10 L acetone for 2–3 Kg bacterial mass) at 2°–8° C. for 24–48 hrs. The acetone is decanted, and the biomass evaporated to remove remaining acetone. The biomass is then suspended in sterile distilled water (1500 ml for 1000 g bacterial mass). Next, 20 L 96% ethanol for each 1 kg bacterial mass is added to the suspended cells. The suspension is maintained under stirring at 60° C. for 30 minutes in a tank.

The ethanol suspension is filtrated through a Seitz T500 filter (3–8 μm pores). The clear filtrate is concentrated to semi-dryness in a rotary evaporator.

The concentration (crude extract) is dissolved in 85% ethanol (200 ml for 1000 g bacterial mass). Three volumes of cold acetone are added to 1 volume of the ethanol solution of crude extract and the mixture is left for 15–20 minutes at −18° C. The acetone-alcohol solution is then centrifuged at 2000 g for 15–20 minutes.

The sediment is suspended in sterile distilled water (1 volume) and two volumes of cold acetone are added. After 15 minutes at −18° C. the mixture is centrifuged at 2000 g for 15–20 minutes. The sediment is suspended again in 1 volume of sterile distilled water and 1 volume of cold acetone is added. The mixture is again centrifuged.

The resultant sediment is suspended in sterile distilled water (a total volume of approximately 500–1000 ml) and sterilized to form a colony modulating factor. This colony modulating factor may be combined with additional buffers, suspending agents, and preservatives.

Preliminary chemical analysis shows the sediment comprises glycolipids and/or phospholipids. Biological activity appears to be due to lipid component(s).

This general method of extraction would isolate the lipid component of bacteria other than *Pseudomonas aeruginosa*. Thus, the method could be applied to the group of bacteria identified herein.

An effective amount of lipid extract derived from *Pseudomonas aeruginosa* comprises 0.1–10.0 mg. Preferably, the amount is in the range of 0.5–1.0 mg. Preferably, the effective amount is administered more than once. Preferably, the effective amount is administered every day to every thirty days and, more preferably, every five to fifteen days. This regimen can be maintained for up to six months to one year, or even the life of a subject. Preferably, the effective amount is administered weekly for up to fifty-two weeks; more preferably, for one to thirty-two weeks, and even more preferably, for four to fourteen weeks.

Preferably, after a period of administration of the lipid extract, the therapy is discontinued for four to 52 weeks and restarted. Even more preferred, the therapy is restarted after eight to fourteen weeks.

A preferred manner of administration of the lipid extract is 0.5–1.0 mg weekly for four to eight weeks and then discontinue administration. This is restarted after a break of four to eight weeks. This cycle of administration and breaks is repeated as necessary.

The effective amount, 0.5–1.0 mg of lipid extract is usually administered in a solution suitable for subcutaneous administration. A typical solution for administration contains 0.5 to 1.0 mg extract/ml with suitable preservatives, buffers and salts. A preferred routine of administration is by subcutaneous injection.

Embodiments of the present invention provide clinical benefits to individuals exhibiting neutropenia or at risk of developing neutropenia. These benefits are highlighted in the Example which follows.

EXAMPLE 1

In this example, individuals exhibiting neutropenia or at risk of neutropenia were treated with a colony modulating factor. This study was an open label, randomized, controlled trial involving 22 subjects. Volunteers who met the inclusion and exclusion criteria and consented to participate in the study were recruited. Since the most common cause of neutropenia is cancer chemotherapy, the principal inclusion criteria was subjects recently diagnosed of chemotherapy sensitive malignancies and who are willing to undergo multiple cycles of chemotherapy regimen.

For the purposes of this study, neutrophil counts of 1,000–1,500 cells/$\mu$L is considered a condition of mild neutropenia. A count of 1,000 cells to 500 cells/$\mu$L is moderate neutropenia and a count of 500 cells/$\mu$L or less is severe neutropenia.

Individuals with neutropenia counts of 1,000 to 1,500 will normally exhibit no significant propensity for infection. These individuals, in the presence of infection, may exhibit fevers which can be managed on an outpatient basis. Individuals with moderate neutropenia may exhibit a propensity to infection. These individuals may exhibit fevers in the presence of infection which are difficult to manage. Individuals with severe neutropenia exhibit a significant propensity to infection. These individuals exhibit fevers in the presence of infection that are normally managed on an inpatient basis with antibiotics.

The subjects were separated into two groups. One group, the test group subjects, received a colony modulating factor, a lipid extract, purchased under the trademark "Cantastim" (Cantacuzino Institute—Bucharest, Romania). Test group subjects were administered 12 weekly subcutaneous injections of the extract. These test group subjects were also administered chemotherapy in three cycles of one month each. The first extract injection was administered before the chemotherapy dosing session; either the same day or 48 hours prior.

The subjects of the control group did not receive any injections other than their chemotherapy drugs. Ten test group subjects were matched with 12 control subjects for drug regimen, cancer types and age.

Routine laboratory investigations were performed at initiation and at several points during the study period. Clinical evaluation and complete blood counts (CBC) were performed twice a week.

Results were analyzed to study the severity, incidence and duration of neutropenia in each group. Severity of neutropenia was measured by calculating the neutropenia ratio. This ratio was defined as the minimum neutrophil count attained during chemotherapy over the predosing value. These data are summarized, in bar graph form, in FIG. 1. FIG. 1 depicts the percent of total subjects in each group at each cycle of chemotherapy exhibiting no symptoms of neutropenia, or mild neutropenia, or moderate to severe symptoms of neutropenia. In FIG. 1, the percent of total subjects without symptoms of neutropenia are depicted by the vertical bars with diagonal lines. The percent of total subjects exhibiting symptoms of mild neutropenia are depicted by the vertical bars with dotted shading. The percent of total subjects exhibiting symptoms of moderate to severe neutropenia are depicted with crosshatched bars.

The results suggest that the total percent of all subjects receiving a colony modulating factor exhibiting neutropenia was lower than those receiving chemotherapy without the colony modulating factor. That is, the colony modulating factor appears to protect some subjects from the effects of chemotherapy. All of the control subjects exhibited symptoms of neutropenia by the third cycle. These results suggest that colony modulating factors are effective in limiting neutropenia in subjects undergoing treatment with myelosuppressive drugs.

Figure 2:
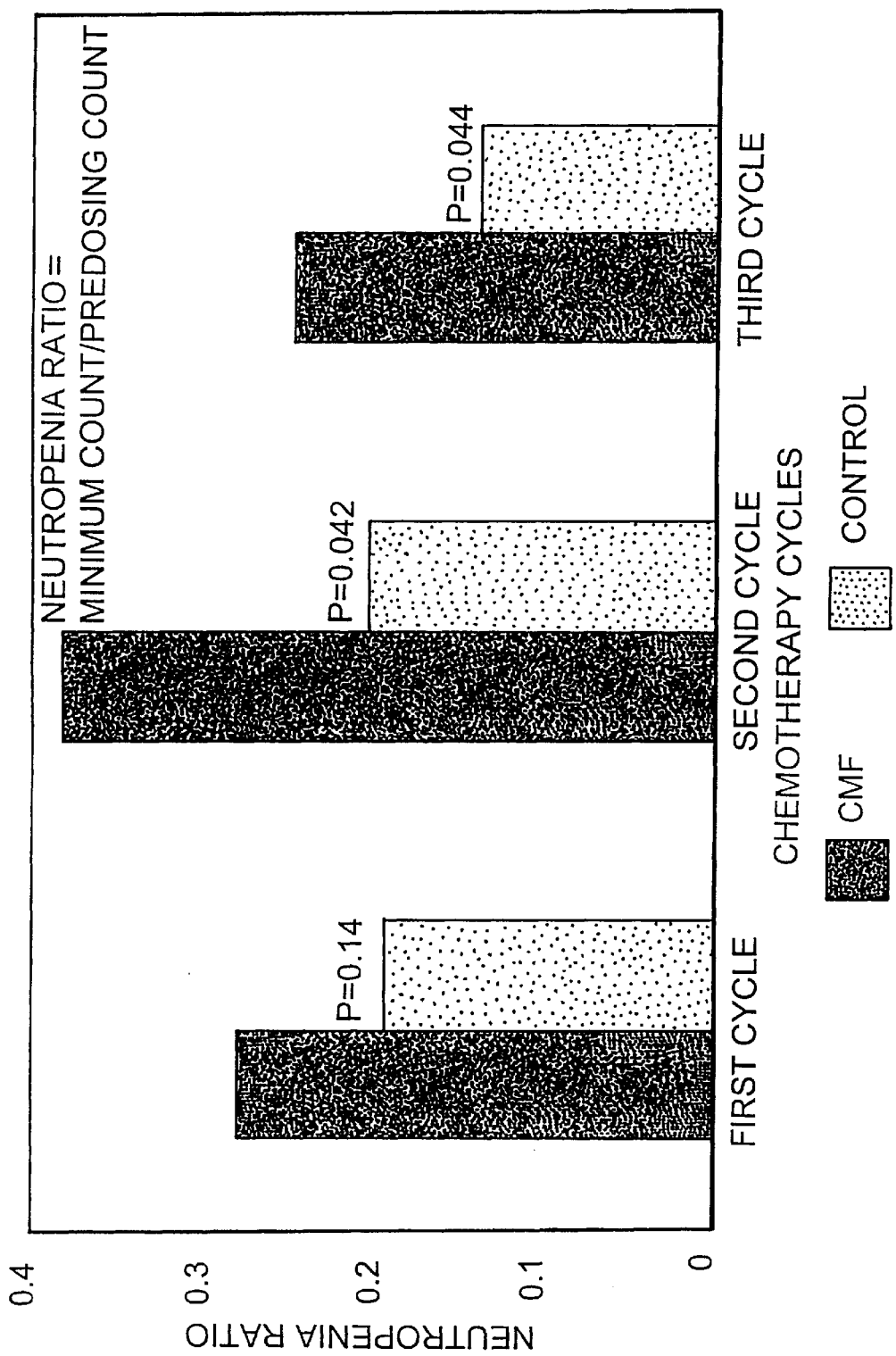
FIG. 2 depicts, in bar graph form, the incidence of mild or moderate/severe neutropenia in cancer chemotherapy patients receiving colony modulating factor therapy in accordance with the present invention.

The neutropenia ratios were significantly lower in control groups as compared to test group in all the three cycles of chemotherapy. These data are summarized, in bar graph form, in FIG. 2. FIG. 2 depicts the neutropenia ratio for each cycle of chemotherapy. Subjects receiving a colony modulating factor are illustrated with a dark shaded bar. Subjects acting as controls are illustrated with light shaded bars. A two tailed t-test revealed statistically significance in second and third cycle (P=0.042 and P=0.044, respectively). The incidence of moderate to severe neutropenia and the duration of neutropenia was higher in control group as compared to the test group. These results are set forth in Table 1.

TABLE 1

EFFECT OF COLONY MODULATING FACTOR ON CHEMOTHERAPY-INDUCED NEUTROPENIA

| Cycle | Trial Group | Predose Mean Neutrophil Counts | Lowest Mean Neutrophil Counts | Mean Neutropenia Ratio* | Neutropenia** None (>1,500) | Mild (1,000–1,500) | Moderate to Severe (<1,000) | Duration of Neutropenia 1 Week or Less | >1 week |
|---|---|---|---|---|---|---|---|---|---|
| First | Control (n = 2) | 5591 ± 1108 | 967 ± 362 | 0.231 | 0.00 | 50% (1244) | 50% (690) | 50% | 50% |
| | ****CMF (n = 10) | 5748 ± 1730 | 1492 ± 924 | 0.354 ***P = 0.14 | 30% (2708) | 30% (1193) | 40% (803) | 50% | 20% |
| Second | Control (n = 12) | 3946 ± 1325 | 759 ± 435 | 0.247 | 8% (1740) | 8% (1400) | 83% (597) | 42% | 20% |
| | ****CMF (n = 10) | 3709 ± 913 | 1330 ± 767 | 0.464 ***P = 0.042 | 40% (2204) | 20% (1089) | 30% (576) | 30% | 30% |
| Third | Control (n = 12) | 3464 ± 520 | 512 ± 229 | 0.155 | 0.00 | 8% (1008) | 92% (448) | 8% | 92% |
| | ****CMF (n = 10) | 3615 ± 1380 | 997 ± 625 | 0.331 ***P = 0.044 | 20% (2006) | 30% (1179) | 50% (483) | 30% | 50% |

*Ratio of the minimum neutrophil count attained during chemotherapy to the predosing value: $\frac{\text{minimum count}}{\text{predosing count}}$

**Expressed as percent of subjects in each category

*** T-test assuming equal variance (two tailed).

****Colony modulating factor

No significant systemic or local adverse events were experienced.

EXAMPLE 2

In this example, healthy individuals were treated with the colony modulating factor utilized in Example 1. This study was an open label, internal controlled, 15 week, safety study involving 14 healthy volunteers. Seven HIV negative male and seven nonpregnant, HIV negative female volunteers with normal blood chemistry, hematology, and urinalysis parameters were recruited for the study. An EKG, X-ray chest, and PPD skin test were performed at the beginning of the study and were repeated at the end of the study. The volunteers were followed up weekly with clinical evaluation, CBC, and urinalysis. Dosing started after a 3 week control period. The colony modulating factor was administered in an amount of 0.5 mg as a 1 mL injection subcutaneously every week for 12 weeks.

An interim analysis of the hematological parameters after seven injections of the colony modulating factor was performed. The analysis did not suggest any statistically significant variation from the normal values. The results are summarized in Table 2 below.

TABLE 2

Effect of Colony Modulating Factor on the WBC and Neutrophil Counts in Healthy Volunteers

| Number of Subjects | Period of Follow-Up | Mean WBC Count | Mean Neutrophil Count |
|---|---|---|---|
| 14 | Control Period (4 time points) | 7790 | 4686 |
| 14 | CMF Period (7 time points) | 7670 | 4928 |
| Two tailed t-test assuming equal variance | | P = 0.86 | P = 0.69 |

The total WBC count as well as the neutrophil count during or after seven injections remained within normal range. Compared with predosing control measurements, p values were 0.69 and 0.86, respectively (two tailed t-test assuming equal variation).

No significant systemic or local adverse events were reported during the follow-up period. These results suggest that the colony modulating factor does not result in over-stimulation of the peripheral blood cell population eliminating the risk of myeloproliferative effects such as leukocytosis or polycythemia.

It will be seen from the foregoing examples that the present methods stabilize the neutrophil count or produce an improvement in individuals exhibiting neutropenia. Individuals receiving the colony modulating factor experience or perceive an improved quality of life. The present method is cost effective. The method of the present invention is affordable, in terms of industrial countries and developing countries. The present method is well tolerated with little or no effect on healthy individuals.

Embodiments of the present invention are capable of modification and alteration which modifications and alterations are within the purview of the present invention as described in the following claims.

We claim:

1. A method of treating neutropenia in a human subject comprising the step of administering to a human subject exhibiting neutropenia or at risk of developing neutropenia a colony modulating factor derived from *pseudomonas* in an amount effective for inhibiting a decrease in the number of neutrophils in the subject, wherein the colony modulating factor is a *pseudomonas* solvent extract which is prepared by the steps of incubating a *pseudomonas* culture with a ketone to produce a first precipitate, wherein the ketone is a lower $C_2$-$C_6$;

mixing the first precipitate with an alcohol to produce an alcohol extract, wherein the alcohol is a lower $C_1$-$C_6$;

collecting the alcohol extract; and precipitating an active material from the alcohol extract with a lower $C_1$-$C_6$ ketone to produce the *pseudomonas* solvent extract.

2. The method of claim 1 wherein said colony modulating factor is administered in an amount effective for increasing the number of neutrophils in the subject.

3. The method of claim 1 wherein said colony modulating factor comprises a mixture of lipids.

4. The method of claim 2 wherein said colony factor modulator comprises a mixture of lipids.

5. The method of claim 3 wherein said lipid mixture comprises glycolipids and/or phospholipids.

6. The method of claim 4 wherein said lipid mixture comprises glycolipids and/or phospholipids.

7. The method of claim 6 wherein said lipid extract is derived from *Pseudomonas aeruginosa*.

8. The method of claim 1 wherein said colony modulating factor is administered subcutaneously.

9. The method of claim 1 wherein said colony modulating factor is administered every day to every thirty days.

10. The method of claim 1 wherein said colony modulating factor is administered every five to fifteen days.

11. The method of claim 10 wherein said colony modulating factor is administered every five to fifteen days for up to 52 weeks.

12. The method of claim 10 wherein said colony modulating factor is administered for up to 32 weeks.

13. The method of claim 10 wherein said colony modulating factor is administered weekly for four to fourteen weeks.

14. The method of claim 3 wherein said effective amount is 0.1–1 mg.

15. The method of claim 7 wherein said effective amount is 0.5 mg.

16. The method of claim 11 wherein said administration of colony modulating factor is discontinued for periods of four to fifty-two weeks and resumed.

17. The method of claim 13 wherein said administration of colony modulating factor is discontinued for a period of eight to fourteen weeks and resumed.

18. The method of claim 5 wherein said lipid extract is derived from *Pseudomonas aeruginosa*.

* * * * *